United States Patent [19]
Torisky et al.

[11] Patent Number: 5,929,306
[45] Date of Patent: Jul. 27, 1999

[54] **KYRT1, A DISARMED VERSION OF A HIGHLY TUMORIGENIC *AGROBACTERIUM TUMEFACIENS* STRAIN IDENTIFIED AS CHRY5**

[75] Inventors: Rebecca S. Torisky, Raleigh, N.C.; Glenn B. Collins, Lexington, Ky.

[73] Assignee: University of Kentucky Research Foundation, Lexington, Ky.

[21] Appl. No.: 08/749,262

[22] Filed: Nov. 15, 1996

[51] Int. Cl.$^6$ .............................. A01H 5/00; C12N 1/21; C12N 5/14; C12N 15/86
[52] U.S. Cl. .................. 800/298; 435/252.2; 435/252.3; 435/320.1; 435/469; 800/278; 800/306; 800/307; 800/312; 800/314; 800/315; 800/317; 800/317.1; 800/317.3; 800/317.4; 800/320.2; 800/322
[58] Field of Search .............................. 435/172.3, 320.1, 435/252.2, 252.3, 469; 800/205, 278, 298, 306, 307, 312, 314, 315, 317, 317.1, 317.3, 317.4, 320.2, 322

[56] References Cited

U.S. PATENT DOCUMENTS 5,416,011  5/1995  Hinchee et al. ..................... 435/172.3

OTHER PUBLICATIONS

Simpson et al. A disarmed binary vector from *Agrobacterium tumefaciens* functions in Agrobacterium rhizogenes. Plant Molecular Biology. 6:403–415, 1986.
E. Hood et al., "New Agrobacterium helper plasmids for gene transfer to plants," *Transgenic Research*, 2: 208–218 (1993).
E. Hood et al., "Virulence of *Agrobacterium tumefaciens* Strain A281 on Legumes," *Plant Physiol.*, 83: 529–534 (1987).
E. Hood et al., "The hypervirulence of *Agrobacterium tumefaciens* A281 is encoded in a region of pTiBo542 outside of T–DNA," *J. Bacteriol.*, 168: 1291–1301 (1986).
Improved antibiotic–resistance gene cassettes and omega elements for *Escherichia coli* vector construction and in vitro deletion/insertion mutagenesis, M. Alexeyev et al., Gene, 160(1995)63–67.
Mini–Tn10 transposon derivatives for insertion mutagenesis and gene delivery into the chromosome of Gram–negative bacteria, M. Alexeyev et al., Gene, 160(1995)59–62.
T–DNA of the Agrobacterium TI and RI Plasmids, M. Bevan et al., Ann. Rev. Genet. 1982, 16:357–84.
Characterization of an Unusual New *Agrobacterium tumefaciens* Strain from *Chrysanthemum morifolium* Ram, A. Bush et al., Applied and Environmental Microbiology, Sep. 1991, pp. 2468–2472.
Strain and cultivar specificity in the Agrobacterium–soybean interaction, M. Byrne et al., Plant Cell, Tissue and Organ Culture 8:13–15 (1987).
Agrobacterium gene transfer: Progress on a "poor man's vector" for maize, M. Chilton, Proc. Nat'. Acad. Sci. USA, vol. 90, pp. 3119–3120, Apr. 1993.

Transgenic analysis of the 5'—and 3' –flanking regions of the NADH–dependent hydroxypyruvate reductase gene from *Cucumix sativus* L, S. Daniel et al., Plant Molecular Biology 28: 821–836, 1995.
The Host Range of Crown Gall, M. Clene et al., The Botanical Review, vol. 42, Oct.–Dec. 1976, No. 4, pp. 389–466.
Mini–Ti: A New Vector Strategy for Plant Genetic Engineer, A. de Framond et al., Bio/technology, May 1983, pp. 262–269.
Broad host range DNA cloning system for Gram–negative bacteria: Construction of a gene bank of *Rhizobium meliloti*, G. Ditta et al., Proc. Natl. Acad. Sci. USA, vol. 77, No. 12, pp. 7347–7351, Dec. 1980.
Production of Agrobacterium–mediated transgenic fertile plants by direct somatic embryogenesis from immature zygotic embryos of *Datura innoxia*, C. Ducrocq et al., Plant Molecular Biology 25: 995–1009, 1994.
Regulation of *Agrobacterium tumefaciens* T–cyt gene expression in leaves of transgenic potato (*Solanum tuberosum* L. cv. Desiree) is strongly influenced by plant culture conditions, D. Dymock et al., Plant Molecular Biology 17: 711–725, 1991.
Identification of unexplained DNA fragments within the T–DNA borders of the Bin 19 plant transformation vector, R. Fray et al., Plant Molecular Biology 25: 339–342, 1994.
Growth Inhibition and Loss of Virulence in Cultures of *Agrobacterium tumefaciens* Treated with Acetosyringone, C. Fortin et al., Journal of Bacteriology, Sep. 1992, pp. 5676–5685.
Construction of a broad host range cosmic cloning vector and its use in the genetic analysis of Rhizobium mutants, A. Friedman et al., Gene, 18 (1982) pp. 289–296.
An essential virulence pf *Agrobacterium tumefaciens*, VirB4, requires an intact mononucleotide binding domain to function in transfer of T–DNA, K. Fullner et al., Mol Gen Genet (1994) 245:704–715.
Expression of a Bacterial Phaseolotoxin–Resistant Ornithyl Transcarbamylase in Transgenic Tobacco Confers Resistance to *Pseudomonas Syringae* pv. Phaseolicola, J. de la Fuente–Martinez et al., Bio/Technology vol. 10, Aug. 1992, pp. 905–909.
DNA Flux Across Genetic Barriers: The Crown Gall Phenomenon, G. Gheysen et al., Plant Gene Research: Genetic Flux in Plants, 1985, pp. 11–47.

(List continued on next page.)

*Primary Examiner*—Gary Benzion
*Assistant Examiner*—Amy J. Nelson
*Attorney, Agent, or Firm*—McDermott, Will & Emery

[57] ABSTRACT

Disarmed *A. tumefaciencs* strain KYRT1, derived from a highly tumorigenic strain identified as *A. tumefaciens* strain Chry5. Disarming is accomplished by inactivation of plasmid pTiChry5 T-DNA sequences by, for example, deletion of sequences comprising the T-DNA right border. Methods of making transgenic plants using the novel *A. tumefaciens* strains are also provided.

5 Claims, 3 Drawing Sheets

OTHER PUBLICATIONS

Illegitimate recombination in plants: a model for T–DNA integration, G. Gheysen et al., Gene & Development 5:287–297, 1991.

The small, versatile pPZP family of Agrobacterium binary vectors for plant transformation, P. Hajdukiewicz et al., Plant Molecular biology 25:989–994, 1994.

Re–evaluation of Conditions for Plant Regeneration and Agrobacterium–Mediated Transformation from Tomato (*Lycopersicon esculentum*), S. Hamza et al., Journal of Experimental Botany, vol. 44, No. 269, pp. 1837–1845, 1993.

Optimization of biolistic transformation of embryogenic grape cell suspensions, D. Hebert et al., Plant Cell Reports (1993) 12:585–589.

Agrobacterium and plant genetic engineering, P. Hooykaas et al., Plant Molecular Biology 19: 15–38, 1992.

Transformation of plant cells via Agrobacterium, P. Hooykaas, Plant Molecular Biology 13: 327–336, 1989.

The Virulence System of *Agrobacterium Tumefaciens*, P. Hooykaas et al., Annu. Rev. Phytopathol. 1994, 32:157–79.

Inheritance of Functional Foreign Gene in Plants, R. Horsch et al., Science, vol. 223, Feb., 1984, pp. 496–498.

A Simple and General Method for Transferring Genes into Plants, R. Horsch et al., Science, vol. 227, Mar. 1985, pp. 1227–1231.

Acetosyringone and osmoprotectants like betaine or proline synergistically enhance Agrobacterium–mediated transformation of apple, D. James et al., Plant Cell Reports (1993) 12:559–563.

Evaluation of a Cotyledonary Node Regeneration System for Agrobacterium–Mediated Transformation of Pea (*Pisum Sativum* L.), M. Jordan et al.

Genetic Analysis of T–DNA Transcripts in Nopaline Crown Galls, H. Joos et al., Cell. vol. 32, 1057–1067, Apr. 1983.

Molecular Mechanisms of Crown Gall Tumorigensis, C. Kado, Critical Reviews in Plant Sciences, 10(1):1–32(1991).

Mapping and genetic organization of pTiChry5, a novel Ti plasmid from a highly virulent *Agrobacterium tumefaciens* strain, L. Kovacs et al., Mol. Gen. Genet(1994) 242:327–336.

The Chromosomal Background of *Agrobacterium tumefaciens* Chry5 Conditions High Virulence on Soybean, L. Kovacs et al., MPMI, vol. 6, No. 5, 1993, pp. 601–608.

The Mechanism of T–DNA Transfer from *Agrobacterium tumefaciens* to the Plant Cell, Z. Koukolikova–Nicola et al.

Multiple copies of virG enhance the transient transformation of celery, carrot and rice tissues by *Agrobacterium tumefaciens*, C. Liu et al.,Plant Molecular Biology 20: 1071–1087, 1992.

Agrobacterium induced gall formation in bell pepper (*Capsicum annuum* L.) and formation of shoot–like structures expressing introduced genes, W. Liu et al., Plant Cell Reports (1990) 9:360–364.

A simple procedure for the expression of genes in transgenic soybean callus tissue, G. Luo et al., Plant Cell Reports (1994) 13:632–636.

Inheritance of Soybean Susceptibility to *Agrobacterium tumefaciens* and its Relationship to Transformation, A. Mauro et al., Crop Sci. 35:1152–1156 (1995).

Susceptibility of some Brazilian soybean genotypes to three strains of *Agrobacterium tumefaciens*, A. Mauro et al., Brazilian Journal of Genetics 18, 3, 417–420 (1995).

Physical and Genetic Characterization of Symbiotic and Auxotrophic Mutants of *Rhizobium meliloti* Induced by Transposon Tn5 Mutagenesis, H. Meade et al., Journal of Bacteriology, Jan. 1982, pp. 114–122.

Plasmids Specifying Plant Hyperplasias, E. Nester, Ann. Rev. Microbiol. 1981, 35:531–65.

Strength and tissue specificity of chimeric promoters derived from the octopine and mannopine synthase genes, M. Ni et al., The Plant Journal (1995), 661–676.

Transformation of Soybean Cells Using Mixed Strains of *Agrobacterium tumefaciens* and Phenolic Compounds, L. Owens et al., Plant Physiol. (1988) 88, 570–573.

Constitutive Mutations of *Agrobacterium tumefaciens* Transcriptional Activator virG, G. Pazour et al., Journal of Bacteriology, Jun. 1992, pp. 4169–4174.

T–DNA border sequences required for crown gall tumorigenesis, E. Peralta et al., Proc. Natl. Acad. Sci. USA, vol. 82, pp. 5112–5116, Aug. 1985.

Petunia plants escape from negative selection against a transgene by silencing the foreign DNA via methylation, S. Renckens et al., Mol. Gen. Genet (1992) 233:53–64.

Inheritance of Rersistance to Crown Gall in *Pisum sativum*, S. Robbs et al., Plant Physiol. (1991) 95, 52–57.

Pathways to Plant Genetic Manipulation Employing Agrobacterium, S. Rogers et al., Plant Gene Research: Plant DNA Infection Agents, 1987, pp. 179–203.

Improved Vectors for Plant Transformation: Expression Cassette Vectors and New Selectable Markers, S. Rogers et al., Methods in Enzymology, vol. 153, pp. 253–277, 1987.

Gene Transfer in Plants: Production of Transformed Plants Using Ti Plasmid Vectors, S. Rogers et al., Methods in Enzymology, vol. 188, pp. 627–641, 1986.

Genetic and Molecular Analsyses of picA, a Plant–Inducible Locus on the *Agrobacterium tumefaciens* Chromosome, L. Rong et al., Journal of Bacteriology, Aug. 1991, pp. 5310–5120.

The right hand copy of the nopaline Ti–plasmid 25 bp repeat is required for tumour formation, C. Shaw et al., Nucleic Acids Research, vol. 12, No. 15, 1984, pp. 6031–6040.

Stimulation of *Agrobacterium tumefaciens* T–DNA Transfer by Overdrive Depends on a Flanking Sequence but Not on Helical Position with Respect to the Border Repeat, C. Shurvinton et al., Journal of Bacteriology, Sep. 1991, pp. 5558–5563.

*Agrobacterium tumefaciens* Transformation of Monocotyledons, R. Smith et al., Crop Sci. 35:301–309 (1995).

La Piste des Opines, J. Tempe et al., Molecular Genetics of the Bacteria–Plant Interaction, 1983, pp. 14–32.

The *Agrobacterium tumefaciens* virC1 Gene Product Binds to Overdrive, a T–DNA Transfer Enhancer, N. Toro et al., Journal of Bacteriology, Dec. 1989, pp. 6845–6849.

Right 25 bp Terminus Sequence of the Nopaline T–DNA is Essential for and Determines Direction of DNA Transfer from Agrobacterium to the Plant Genome, K.Wang et al., Cell, vol. 38, 455–462, Sep. 1984.

Intergenic transfer and exchange recombination of restriction fragments cloned in pBR322: a novel strategy for the reversed genetics of the Ti plasmids of *Agrobacterium tumefaciens*, E. Van Haute et al., The EMBO Journal, vol. 2, No. 3, pp. 411–417, 1983.

*Agrobacterium tumefaciens*–Mediated Transformation of Recalcitrant Crops, M. van Wordragen et al., Plant Molecular Biology Reporter, vol. 10(1) 1992, pp. 12–36.

Virulence Genes, Borders, and Overdrive Generate Single-Stranded T-DNA Molecules from the A6 Ti Plasmid of *Agrobacterium tumefaciens,* K. Veluthambi et al., Journal of Bacteriology, vol. 170, No. 4, Apr. 1988, pp. 1523–1532.

Two-Way Chemical Signaling in Agrobacterium–Plant Interactions, S. Winans, Microbiological Reviews, Mar. 1992, pp. 12–31, vol. 56, No. 1.

Improved M13 phage cloning vectors and host strains: nucleotide sequences of the M13mp18 and pUC19 vectors, C. Yanisch-Perron, Gene, 33(1985), pp. 103–119.

Basic Processes Underlying Agrobacterium–Mediated DNA Transfer to Plant Cells, P. Zambryski, Annu. Rev. Genet. 1988, 22:1–30.

Agrobacterium–Plant Cell DNA Transfer, P. Zambryski, Mobile DNA (1989), pp. 309–333.

Transfer of T-DNA from Agrobacterium to the Plant Cell, J. Zupan et al., Plant Physiol. (1995) 107: 1041–1047.

Chronicles from the Agrobacterium–Plant Cell DNA Transfer Story, P. Zambryski, Annu. Rev. Plant Physiol. Plant Mol. Biol. 1992, 4:465–90.

Ti plasmid vector for the introduction of DNA into plant cells without alteration of their normal regeneration capacity. P. Zambryski et al., The EMBO Journal, vol. 2, No. 12, pp. 2143–2150, 1983.-

KYRT1, A DISARMED VERSION OF A HIGHLY TUMORIGENIC *AGROBACTERIUM TUMEFACIENS* STRAIN IDENTIFIED AS CHRY5

TECHNICAL FIELD

The invention relates to novel disarmed *Agrobacterium tumefaciens* vectors useful for the transformation of plants. More particularly, the invention relates to disarmed *A. tumefaciens* vectors, methods of their use and transgenic plants, particularly dicotyledonous transgenic plants, created thereby. Yet more particularly, the invention relates to disarmed *A. tumefaciens* strain designated KYRT1 and methods of its use and transgenic soybean plants made thereby.

BACKGROUND ART

Soybean is an agronomically important crop. Despite this importance, however, there is only limited breeding potential in the United States due to a small germplasm base. As a result, tremendous efforts have been expended in developing techniques to modify soybean characteristics through the use of genetic engineering. Such modifications offer the possibility of developing plant lines that have specific, tailor-made beneficial traits, such as herbicide resistance, drought resistance, heat resistance, disease resistance, seed quality improvement, and the like, in ways not possible using traditional breeding techniques. Due to the successes of *Agrobacterium tumefaciens*-mediated gene transfer in other plant species, much effort has been placed on developing such a system for the genetic modification of soybean. To date, however, these efforts have met with only limited success, with generally low transformation efficiencies on most soybean cultivars.

*Agrobacterium tumefaciens* is a gram-negative soil bacteria that causes the crown gall disease in plants by infecting cells through wound sites. *A. tumefaciens* infects by injecting into the cell a strand of DNA (termed T-DNA) derived from the large tumor-inducing (Ti) plasmid (van Larebeke et al., *Nature* 255: 742–743, 1975). The T-DNA then integrates into a chromosomal location in the plant and produces enzymes that synthesize hormones which cause the crown gall symptoms (Chilton et al., *Cell* 11: 263–271, 1977). The genes encoding these enzymes, and the eukaryotic regulatory control elements associated therewith, are located on the T-DNA. In addition, the integrated T-DNA also encodes products that direct the synthesis of compounds known as opines, which are amino acid and sugar derivatives, which varies depending upon the *A. tumefaciens* strain.

Mobilization of the T-DNA requires that the products of genes located elsewhere on the Ti plasmid, called collectively the vir genes, which are activated by certain elicitors from the wounded plant cells in trans to synthesize and transfer a single-stranded copy of the T-DNA (the T-strand) to the plant cell (Zambryski, *Ann. Rev. Plant. Physiol. Plant Mol. Biol.* 43: 465–490, 1992; Zupan and Zambryski, *Plant Physiol.* 107: 1041–1047, 1995). The T-DNA sequence on the Ti plasmid is flanked by short 24-bp direct repeats (Yadav et al., *Proc. Natl. Acad. Sci.* (USA), 1982), which are required for the recognition of the T-DNA (Wang et al., *Cell* 38: 455–462, 1984). Sequences immediately surrounding these borders appear to be involved in the polarity of T-strand synthesis, which initiates at the right border (Wang et al., *Mol. Gen. Genet.* 210: 338–346, 1987).

The discovery of the mechanism by which *A. tumefaciens* infects plant cells, i.e. by DNA transfer, led to the realization that this microorganism might be useful, via its Ti plasmid, for transferring agronomically useful genes to plants. Recently it has been demonstrated that foreign DNA, flanked by T-DNA border sequences, can be transferred into plant cells using *A. tumefaciens* as the vector (Hernalsteens et al., *Nature* 287:654–656, 1980). Furthermore, inactivation or removal of the native T-DNA genes involved in hormone synthesis would render the *A. tumefaciens* incapable of producing the crown gall disease symptoms. This process of inactivating or removing genes responsible for disease symptoms is termed "disarming."

The first methods of *A. tumefaciens* engineering involved the simultaneous disarming and introduction of the desired gene, since the introduced gene directly replaced the genes in the T-DNA. By a method termed "homogenotization" (Matzke and Chilton, *J. Mol. Appl. Genet.* 1: 39–49, 1981), the native T-DNA of the Ti plasmid was replaced with a desired gene for transformation. Homologous recombination occurred between the T-DNA of the Ti plasmid and an intermediate construct in a broad host range plasmid, containing the desired gene and a selectable marker (e.g., drug resistance) flanked by T-DNA sequences. The recombination event was forced by a subsequent introduction of a second broad host range plasmid incompatible to the intermediate construct, and selecting for drug-resistance encoded by the selectable marker gene of the introduced T-DNA in the desired construct, and the drug-resistance gene on the incompatible plasmid.

Another strategy developed for engineering *A. tumefaciens* involved cloning the desired gene into a cointegrative intermediate vector, which contained a single region of T-DNA homology and a single border sequence. In this system, the sequences are recombined by a single-crossover event (Horsch et al., *Science* 227: 1229–1231, 1985), which results in the entire vector, including the gene of interest, being integrated. Cointegrative systems pair in regions of homology between the T-DNA region of the Ti plasmid and the DNA sequence on the introduced integrative vector.

One example of a useful cointegrative plasmid is pGV3850, a Ti plasmid from a nopaline strain (C58), from which the entire T-DNA region between the borders was replaced with pBR322, thus offering a recombination site for any gene construct containing pBR322 homology (Zambryski et al., *EMBO J.* 2(12): 2143–2150, 1983).

Upon the discovery that T-DNA does not have to be on the same plasmid as the vir genes (de Framond et al., *Bio/Technol.* 1: 262–269, 1983; Hoekema et al., *Nature* 303: 179–180, 1983), the binary vector was developed. A binary vector is maintained in the *A. tumefaciens* separate from the Ti plasmid, and contains the gene of interest and a selectable marker gene between T-DNA border sequences. These vectors offer a great degree of flexibility, since they do not require a specifically engineered Ti plasmid with a homologous recombination site. For that reason, any disarmed *A. tumefaciens* strain can be used to transfer genes for any binary vector. Owing to their versatility, binary vectors are currently the preferred intermediate vectors for cloning genes destined for *A. tumefaciens*-mediated transfer into plants. However, any *A. tumefaciens* strain to be used with binary vectors must have its own Ti plasmid disarmed, especially if the target plant species is inefficiently transformed via *A. tumefaciens*. Otherwise, the desired gene from the binary vector will be co-transformed with the oncogenic phytohormone genes from the native T-DNA of the bacteria, thereby reducing transformation efficiency of the desired gene and also producing the tumorigenic disease symptoms in many of the target cells and thereby preventing the differentiation of these cells into normal plants.

Disarming wild-type *A. tumefaciens* strains for general use with binary vectors has involved, in some cases, a form of homogenotization. An intermediate construct containing a marker gene flanked by Ti plasmid sequences that are homologous to regions that lie outside the T-DNA, is introduced into the wild-type *A. tumefaciens* by bacterial conjugation (Hood et al., *J. Bacteriol.* 168(3): 1291–1301, 1986; Hood et al., *Transgenic Res.* 2: 208–218, 1993). Whereas disarmed *A. tumefaciens* strains typically have their entire T-DNA sequences removed, it has also been demonstrated that T-DNA mobilization can be inactivated by removal of the right border sequence: reports from work with nopaline-type strains of *A. tumefaciens* show that the right border of T-DNA is necessary for gene transfer, whereas the left border is not. (Joos et al., *Cell* 32: 1057–1067, 1983; Peralto and Ream, *Proc. Natl. Acad. Sci.* (USA), 1985; Shaw et al., *Nucleic Acids Res.*, 12: 6031–6041, 1984; Wang et al., *Mol. Gen. Genet.* 210: 338–346, 1984).

*A. tumefaciens* has a diverse dicot host range, and additionally some monocot families (De Cleene and De Layk, *Bot. Rev.* 42 (4): 389–466, 1976). There are several different strains of *A. tumefaciens*, each classified into octopine-type, nopaline-type, and L,L-succinamopine-type, named after type of opine synthesized in the plant cells they infect. These strains have comparable, although not identical, host ranges and disarmed versions of many types of *A. tumefaciens* have been used successfully for gene transfer into a variety of plant species. (van Wordragen et al., *Plant Mol. Biol. Rep.* 10: 12–36, 1992; Hood et al., *Transgenic Res.* 2: 208–218, 1993). Although its most sensitive hosts are members of the dicot family Solanaceae, *A. tumefaciens*, as mentioned above, has also been demonstrated to infect some monocots as well (Smith and Hood, *Crop Sci.* 35(2): 301–309, 1995).

However, soybean (*Glycine max* L. Merr.) has proven to be very difficult to transform with *A. tumefaciens*, at least in part because it is refractory to infection by wild-type *A. tumefaciens*. Comparative studies with a number of soybean cultivars and *A. tumefaciens* strains suggest that soybean susceptibility to *A. tumefaciens* is limited, and is both cultivar- and bacterial strain dependent (Bush and Pueppke, *Appl. Environ. Microbiol.* 57(9): 2468–2472, 1991; Byrne et al., *Plant Cell Tiss. Org. Cult.* 8: 3–15, 1987; Hood et al., *Plant Physiol.* 83:529–534, 1987). The problems with soybean recalcitrance to *A. tumefaciens* are further complicated by the difficulty of working with soybean in tissue culture.

Progress in *A. tumefaciens*-mediated gene transfer in soybean is limited by two major factors: (1) development of a soybean tissue culture system that efficiently regenerates plants from a single-cell origin (Cheng et al., *Plant Sci. Let.* 19: 91–99, 1980; Wright et al., *Plant Cell Rep.* 5: 150–154, 1986), and (2) further understanding of the mechanism for *A. tumefaciens*-mediated gene transfer, i.e., the fact that certain chemical elicitors applied externally (e.g., acetosyringone) can stimulate vir gene activation and T-DNA transfer into cells of non-host plants such as soybean (Owens and Smigocki, *Plant Physiol.* 88: 570–573, 1988; Stachel et al., *Nature* 318: 624–629, 1985).

One system for soybean *A. tumefaciens*-mediated gene transfer has now been established, and is in wide use (Townsend, International Patent Application WO 94/02620, 1994; Hinchee and Conner-Ward, U.S. Pat. No. 5,416,011, 1995). Despite these advances to date, however, *A. tumefaciens*-mediated gene transfer into soybean remains inefficient and labor-intensive, and methods for improving that efficiency are continually being sought.

As mentioned earlier, some *A. tumefaciens* strains infect soybean more readily than others. One strain, A281, is a supervirulent, broad host-range, L,L-succinamopine-type *A. tumefaciens* strain that shows high virulence on soybean. Strain A281 has a nopaline-type C58 chromosomal background, containing the L,L-succinamopine-type Ti plasmid, pTiBo542, and out-performs its chromosomal and Ti plasmid progenitors on soybean (Hood et al., *Plant Physiol.* 83: 529–534, 1987). Disarming this strain has produced EHA101 and EHA105, strains now widely used in conjunction with soybean transformation (Hood et al., *J. Bacteriol.* 168(3): 1283–1290, 1986; Hood et al., *Plant Physiol.* 83: 529–534, 1987).

Recently, Chry5, another L,L-succinamopine-type strain of *A. tumefaciens* recovered from chrysanthemum, has been found to have a broad host range, and is also highly virulent on soybean (Bush and Pueppke, *Appl. Environm. Microbiol.* 57(9): 2468–2472, 1991). The Ti plasmid of this strain, designated pTiChry5, is comparable in arrangement and homology to pTiBo542 in supervirulent strain A281. The Chry5 strain also possesses a cryptic plasmid, the purpose of which is unclear. Based on stem inoculation assays, Chry5 rivals A281 (Hood et al., *Plant Physiol.* 83: 529–534, 1987) for tumorigenicity on soybean.

The sequences of pTiChry5 have been subcloned as partial EcoRI fragments into a cosmid library in pLAFR1 (Friedman et al., *Gene* 18: 289–296, 1982), and mapped for EcoRI and BamHI sites and for vir, inc, L,L-succinamopine utilization, and the T-DNA regions, based on homology to pTiBo542 of A281. Observations from complementation analysis suggest key cis-acting elements in pTiChry5 near the T-DNA right border as being involved with supervirulence. However, studies involving transferring pTiChry5 into other *A. tumefaciens* strains suggest that there may also be chromosomal involvement in the hypervirulence of Chry5 observed with soybean (Kovacs and Pueppke, *Mol. Gen. Genet.* 242: 327–336, 1994).

U.S. Pat. No. 5,416,011 discloses a method for the transformation of soybean, with a disarmed strain of *A. tumefaciens* designated A208. The β-glucuronidase gene under the control of the cauliflower mosaic virus (CMV) 35S promoter is disclosed as being useful for the determination of transformation efficiency.

International Patent Application WO 94/02620 discloses transformation of soybean using a disarmed *A. tumefaciens* designated LBA 4404 and the induction of bacterial virulence by culture in media having a pH below 6.0.

Kovacs and Peuppke (*Mol. Gen. Genet.* 242: 327–336, 1994) discloses the genomic organization and restriction endonuclease mapping of the Ti plasmid pTiChry5. That publication further discloses that *A. tumefaciens* Chry5 is a highly tumorigenic strain that has the ability to transform soybean.

Kovacs et al. (*Mol. Gen. Genet.* 242: 327–336, 1993) disclose that a cryptic plasmid and the bacterial chromosome of strain Chry5 potentiate the tumorigenic ability of several different Ti plasmids in comparison to their normal genetic background.

Kovacs and Peuppke (*Phytopathology*, 81 (10): Abstract No. 678B, 1991) briefly describes a plasmid-cured *A. tumefaciens* derivative of Chry5 into which the Ti plasmid of strain T37 was conjugated.

Bush and Pueppke (*Appl. Environm. Micorbiol.* 57(9): 2468–2472, 1991) discusses the characterization of *A. tumefaciens* Chry5, isolated from naturally-occurring crown galls on *Chrysanthemum morifolium*. Strain Chry5 is thought to be a biotype I strain that transforms at least 10 different plant species.

Hood et al. (*Transgenic Res.* 2:208–218, 1993) discloses the disarming of three Ti plasmids: one each of the octopine, nopaline and L,L-succinamopine types. *A. tumefaciens* strains A281 and EHA101 are disclosed as able to transform soybean. The disarming derivative of plasmid pTiBo542 from strain A281 is disclosed and designated pEHA105.

Hinchee et al. (*Gene Manipulation in Plant Improvement II, pp.* 203–212, J P Gustafson, ed., Plenum Press, New York, 1990) discusses transformation of soybean by *A. tumefaciens*, wherein out of 100 cultivars of soybean tested for transformation, only three were found susceptible in repeated tests. Also reported is a β-glucuronidase gene marker system.

Kudirka et al. (*Can. J. Genet. Cytol.* 28: 808–817, 1986) discloses various characteristics of wound repair in the presence of tumorigenic and non-tumorigenic strains of *A. tumefaciens* and that soybean explants had recently been transformed.

From these prior disclosures, it is readily apparent that the art would significantly advance with the addition of novel strains of disarmed *A. tumefaciens* having a wide host-range and the ability to more efficiently transform plants, such as soybean, that have here-to-date been refractory to Agrobacterium-mediated transformation. Moreover, since *A. tumefaciens* strains vary somewhat in their host range, creating new disarmed strains is expected to expand the list of *A. tumefaciens*-transformable plant species.

It is thus one object of the invention to provide novel disarmed *A. tumefaciens* strains that are efficient in the transformation of economically important crops, in particular soybean. Another object of the invention is to provide novel methods for increasing the efficiency of *A. tumefaciens*-mediated gene transfer, again particularly with respect to soybean. In conjunction with the foregoing, it is another object of the invention to provide novel genetically engineered Ti plasmids useful in the transformation of both dicots and monocots. Yet another object of the invention is to provide novel methods for the transformation of plants, particularly soybean. A further object of the invention is to provide transgenic plants possessing one or more genetically engineered desirable characteristics. These and other objects of the invention, apparent from the disclosure herein, are realized in the *A. tumefaciens* strains, exemplified by strain KYRT1, under the practice of the invention.

SUMMARY OF THE INVENTION

The invention provides for disarmed strains of *A. tumefaciens*. The invention further provides for disarmed *A. tumefaciens* derived from strain Chry5, wherein the plasmid pTiChry5 has a disarming mutation, such as deletion in part or all of the T-DNA. The invention also provides for a disarmed *A. tumefaciens* designated KYRT1, and derivatives thereof, which is particularly tumorigenic in dicots including, for example, soybean, tomato and collard. The invention additionally provides methods for the efficient transformation of plants, and in particular soybean. The invention also provides for transgenic plants transformed via *A. tumefaciens* KYRT1 or derivatives thereof.

The invention is exemplified by *A. tumefaciens* strain KYRT1, which is an avirulent version of *A. tumefaciens* Chry5, a highly tumorigenic strain on soybean. Disarming is accomplished by removing an approximately 18-kb BamHI fragment of the 285-kb plasmid pTichry5, including approximately 3 to 4-kb of the oncogenic T-DNA and the right border. The deletion is accomplished by first removing the corresponding 18-kb region by BamHI digestion from a 24-kb cloned fragment of pTiChry5 in cosmid pLAFR1, and replacing it with a gene conferring antibiotic (carbenicillin) resistance. The resulting construct is introduced into *A. tumefaciens* Chry5 by bacterial conjugation and a homologous recombinant between the construct and pTiChry5 is selected for by the subsequent conjugation of the incompatible group P plasmid pPH1JI. The resulting recombinant *A. tumefaciens* strain was named KYRT1. The transformation efficiency of KYRT1 and comparative examples (including EHA105) is assayed by inoculating soybean (cv. Fayette) cotyledonary node explants. On average, KYRT1 produced many more transformed multicellular sectors than the comparative strains, demonstrating that KYRT1 is equally or more effective than the comparative strains (EHA105 and GV3850) at delivering DNA into soybean in a binary vector system.

DETAILED DESCRIPTION OF THE INVENTION

Soybean is difficult to transform by engineered (i.e., disarmed) *A. tumefaciens*-mediated gene transfer. Nevertheless, *A. tumefaciens* is the preferred system for gene transfer since, with a susceptible host plant, it integrates foreign DNA into the host genome with high efficiency and without the degree of rearrangement or truncation that typically occurs with direct DNA transfer methods, such as particle bombardment and electroporation. Therefore, a disarmed version of any strain that shows a strong capacity for virulence on soybean represents a welcome breakthrough in the field of soybean genetic engineering.

The invention thus provides for *A. tumefaciens* strain KYRT1 to fulfill the need in the art and the objectives set forth above. *A. tumefaciens* KYRT1 is a disarmed derivative of the broad host range vector *A. tumefaciens* Chry5, which itself is highly tumorigenic on soybean.

Figure 1A:
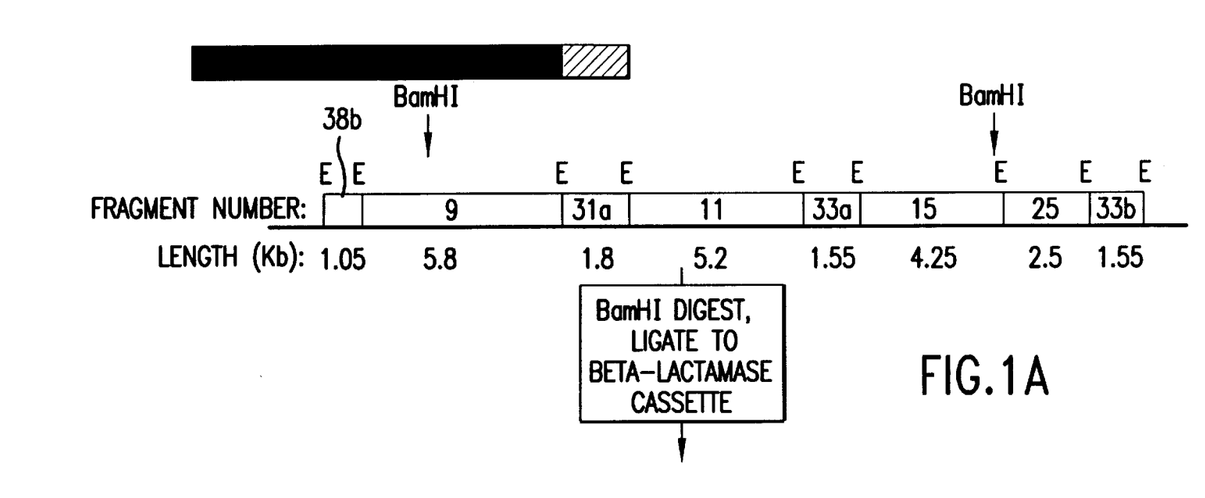
FIGS. 1A–1C: Construction of PCH1B, triparental mating. (A) depicts an EcoRI map of pTiChry5 subclone pCH77 showing the approximate locations of the oncogenic T-DNA (black bar) and the right border sequence (hatched bar) (Kovacs and Peuppke, Mol. Gen. Genet. 242: 327–336, 1994). (B) depicts a map of pCH1B, containing the β-lactamase insert from pBSL167 (Alexeyev, M. F, et al., Gene 160(1): 63–67, 1995), with restriction sites for EcoRI (E) and BamHI (B) marked. (C) presents a summary of the two triparental mating steps to disarm Chry5, resulting in homologous recombination between pCH12 and pTiChry5. The detailed insert of pTiChry5 shows the relative positions of overlapping subclones pCH23 and pCH77, and the oncogenic T-DNA. BamHI sites and fragment numbers are also indicated.
Figure 1B:
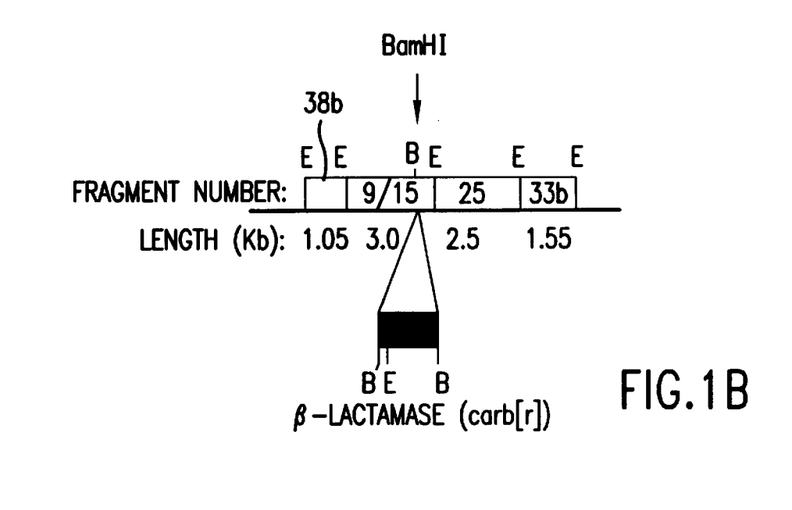
Figure 1C:
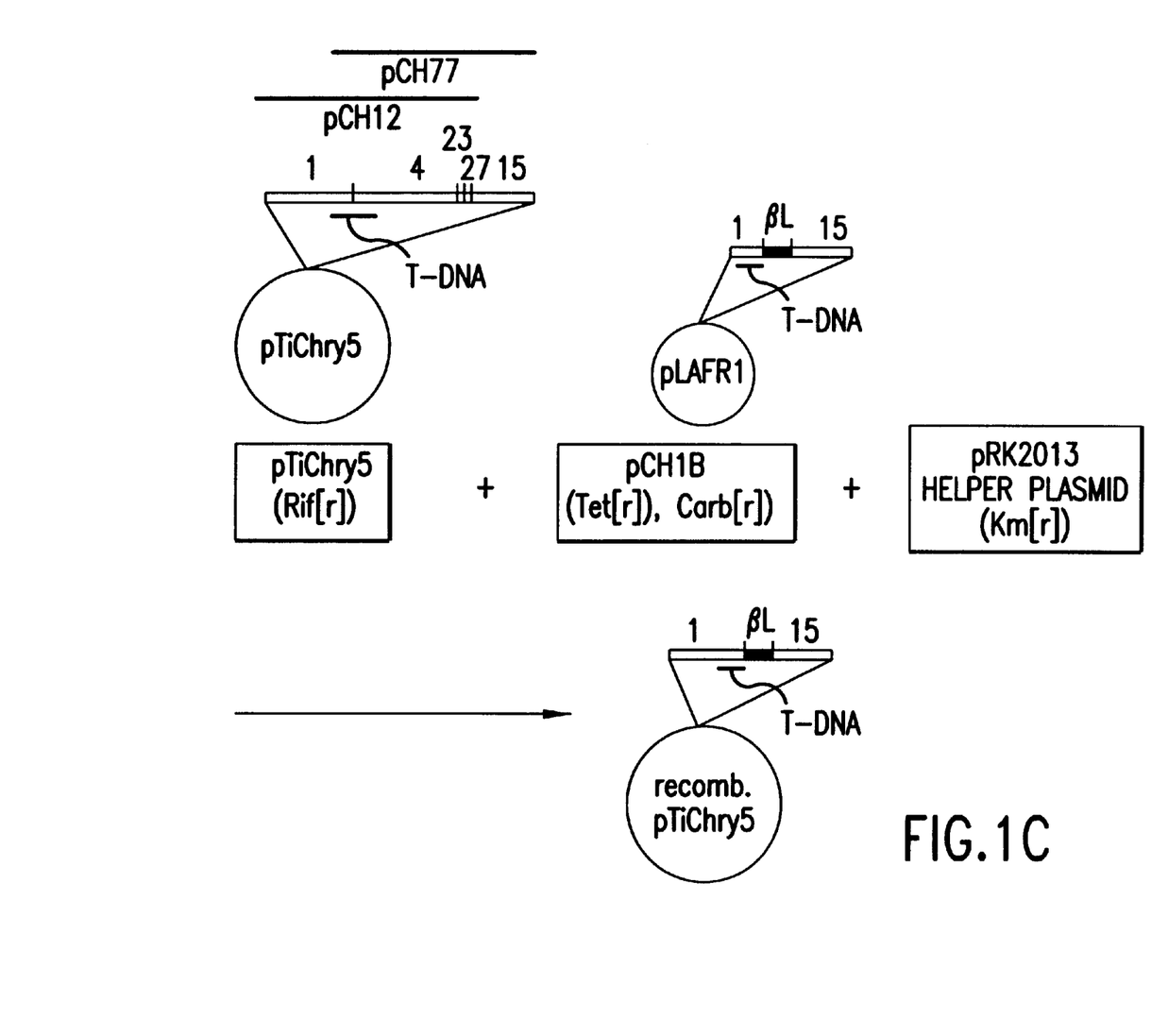

Disarming of *A. tumefaciens* strain Chry5 was accomplished by removing approximately 18-kb of the bacterium's tumor-inducing (Ti) plasmid (pTiChry5), which included 6-kb of the oncogenic sequences comprising the transfer DNA (T-DNA), which during infection is mobilized into the plant cell by the bacteria to generate the crown gall symptoms. The deleted sequences also include a short signal sequence called a border, which is essential for the mobilization of the T-DNA. The deletion was accomplished by first removing the corresponding 18-kb region by BamHI endonucleolytic digestion of plasmid pCH77, which itself comprises a 24-kb fragment of the Ti plasmid (pTiChry5) of *A. tumefaciens* strain Chry5 cloned in the broad host-range vector pLAFR1 (Friedman et al., Gene 18: 289–296, 1982) (FIG. 1A). The deleted fragment was replaced with a marker gene, the β-lactamase gene, which confers resistance to the antibiotic carbenicillin (FIG. 1B). The resulting construct, designated pCH1B, thus contained the β-lactamase gene flanked on each side by approximately 4-kb of Ti plasmid sequence.

Figure 2A:
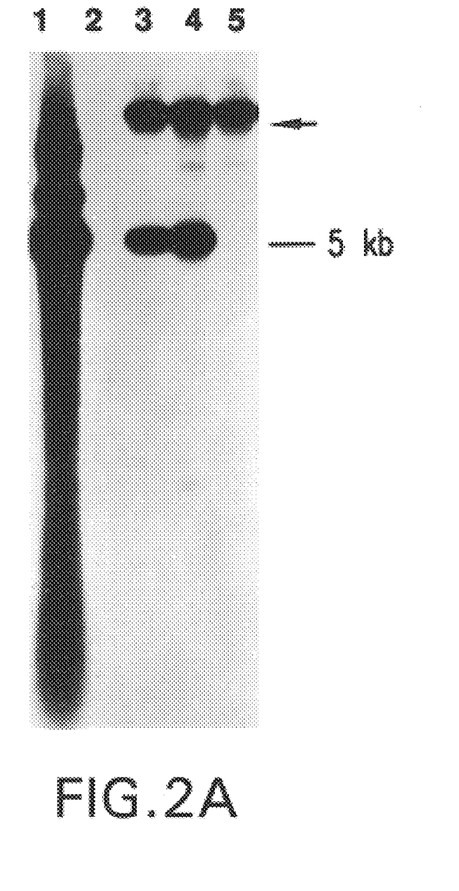
FIGS. 2A–2B: Southern Analysis of total DNA of Chry5, Chry51B and KYRT, with probes of pTiChry5 T-DNA region. Total DNA of Chry5, Chry51B and KYRT, and cosmid DNA of pCH77 and PCH1B, were digested with EcoRI and the fragments were separated by agarose (0.8% TAE) electrophoresis (10 μg/lane genomic DNA, approximately 1 μg/lane pCH77 DNA and 0.1 μg/lane pCH1B DNA). Southern hybridization was conducted at 65° C. using labelled probes of (A) subcloned pTiChry5 EcoRI fragment 11 and (B) subcloned EcoRI fragment 9. Lanes are: (1) cosmid clone pCH77, (2) intermediate construct pCH1B, and total DNA of (3) wild-type Chry5, (4) Chry51B, and (5) KYRT. Arrow indicates the position of the chromosomal fragment homologous to pTiChry5 EcoRI fragment 11.
Figure 2B:
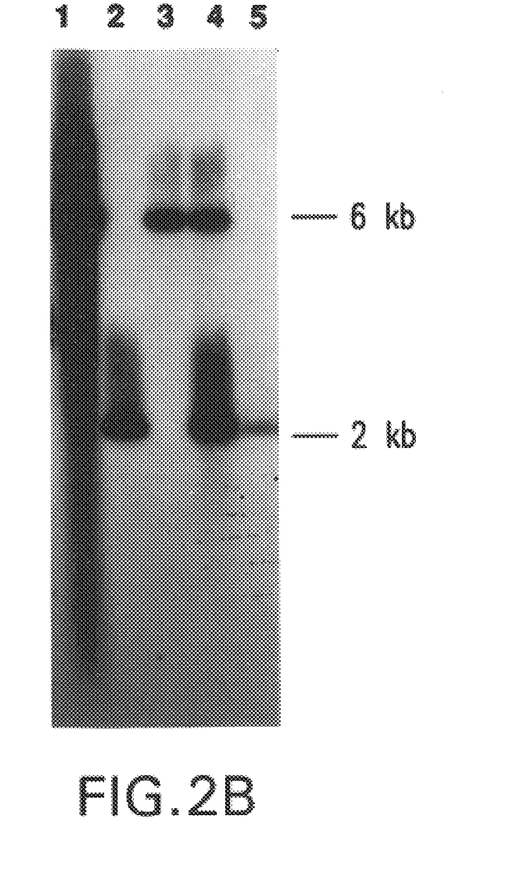

Cosmid pCH1B was then introduced into *A. tumefaciens* strain Chry5 by bacterial conjugation generating Chry51B (see below). Homologous recombination between pCH1B and pTiChry5 was forced by the introduction of plasmid pPH1JI (Hirsch and Berenger, *Plasmid* 12: 139–141, 1984), which is incompatible with plasmid pLAFR1. The recombinant, KYRT1, was identified by resistance to carbenicillin, rifampicin (the selection marker for *A. tumefaciens* strain Chry5), and gentamicin, a selection marker for pPH1JI (FIG. 2). Bacteria surviving this selection are expected to have the β-lactamase gene integrated by homologous recombination into pTiChry5 in place of the deleted 18-kb T-DNA sequence, contain the free-living pPH1JI, and to have lost pCH1B in the free-living cosmid pLAFR1, which rendered the strain tetracycline-sensitive.

Southern analysis was performed confirming the results of the selection procedure, in which the genomic and Ti plasmid DNA of *A. tumefaciens* KYRT1 rendered the expected results. The loss of the ability of the selected product to form tumors on tomato and tobacco stems, compared with the Chry5 wild-type progenitor (Table 1), further confirmed that the 18-kb of T-DNA had been deleted from *A. tumefaciens* Chry5.

The use of strain KYRT1 with binary vectors having an RK2 origin of replication is not hindered by the presence of pPH1JI, which would be expelled by the introduction of, and selection for, that binary vector. This was demonstrated by introducing a binary vector (pBI121) containing an intron-containing β-glucuronidase (GUS-INT) into *A. tumefaciens* KYRT1. The binary vector conferred kanamycin-resistance to the resulting strain. This strain was also gentamicin sensitive due to the loss of pPH1JI. Tobacco leaf pieces inoculated with KYRT1::GUS-INT produced GUS-transformed calli on culture medium containing hormones and kanamycin. These calli formed shoots, which were grown into normal rooted plants. Importantly, leaf pieces inoculated with KYRT1::GUS-INT formed no callus when cultured on hormone-free medium, implying that the T-DNA, which contains genes for phytohormone synthesis in infected tissue, had been effectively rendered non-functional in KYRT1. Conversely, tissue inoculated with wild-type Chry5::GUS-INT generated callus on both hormone-containing and hormone-free media, which assaying positive for expression of the GUS-INT gene.

It will be appreciated that while the preferred plant species for transformation is soybean (*Glycine max*), other species may also be used. These include those of the genus Medicago, Lycopersicon, Brassica, Cucumis, Solanum, Juglans, Gossypium, Malus, Vitis, Antirrhinum, Populus, Fragaria, Arabidopsis, Picea, Capsicum, Chenopodium, Dendranthema, Pharbitis, Pinus, Pisum, Oryza, Glycine, Pseudotsuga, Vinis, Kaleanchoe, Beta, Helianthus and Nicotiana. Conifers are also preferred.

The invention as described herein is exemplified by the deletion of T-DNA sequences between two BamHI restriction sites in order to disarm the bacterium. However, it will be appreciated that other disarming mutations of wide host-range, highly tumorigenic Ti plasmids such as pTiChry5 may be used in the practice of the invention. Indeed, it is only necessary, in the case of a deletion, that sufficient T-DNA and/or border DNA be removed to provide the disabled phenotype. Moreover, disarming mutations other than deletions may be used under the practice of the invention, including (but not limited to), point mutations and insertions as well as combinations of these mutational methods.

The invention is exemplified below using the cotyledon and leaf regeneration system for the production of soybean and tobacco, respectively. However, other regeneration systems known in the art may be used as well. These include the cotyledonary node, immature embryo and protoplast regeneration systems as well as others known to those skilled in the art.

The selection of transformed tissue is most usually accomplished in plant regeneration by inserting an antibiotic resistance gene into the transformed tissue. There is a large number of such antibiotics useful for this purpose including, for example, rifampicin, carbenicillin, chloramphenicol, ampicillin, gentamicin, kanamycin, tetracycline, 2(N-Morpholine)ethanesulfonic acid (MES), hygromycin. Non-antibiotic selective agents, such as methotrexate, may also be employed.

As pertaining to *A. tumefaciens* KYRT1 and its derivatives and obvious variants, the invention is not meant to be limited to soybean transformation, as these vectors are thought to be useful in the transformation of a wide variety of dicotyledonous and/or monocotyledonous plants. Accordingly, while soybean is the preferred plant species, the practice of the methods of the invention and the claims appended hereto are not meant to be limited in scope or spirit to any particular plant species.

The utility of the present invention is well apparent to those skilled in the art, for it is widely known that soybean is a major food and feed source and any improvements therein under the practice of the invention will serve to further increase the agronomic value of this plant. Moreover, as discussed above, due to a limited genetic diversity, the techniques and vectors of the invention allow for the generation of novel plant characteristics that have heretofore not been possible to attain by traditional breeding methods.

The desirable characteristics that may be imparted on plants, particularly soybean, under the practice of the invention include, but are not limited to, resistance to water stress, resistance to heat stress, resistance to cold stress, resistance to one or more insect pests, resistance to pesticides, increased yield and increased nutritional content.

It should also be appreciated that the *A. tumefaciens* and methods of the present invention may be used to create plants that act as a biofactory, producing any number of desirable compounds. In this regard, production of pharmaceutically active compositions, such as peptide hormones, etc., and other useful protein(s) and polypeptides, including mammalian and human proteins and polypeptides, may be produced in large quantity and at reduced cost.

What follows hereinafter are exemplary embodiments of the invention, wherein the preparation of a novel *A. tumefaciens*, KYRT1, and its use in the generation of transgenic soybean is disclosed.

METHODS

Construction of pCH1B

Cosmid clone pCH77 contains a 24 kb fragment of pTiChry5 DNA including the oncogenic T-DNA and right border in the pLAFR1 cosmid (Kovacs and Peuppke, *Mol. Gen. Genet.* 242: 327–336, 1994). This clone was digested with BamHI and the vector sequences isolated by agarose gel electrophoresis. Plasmid pBSL167 (Alexeyev, M. F., et al., *Gene* 160(1): 63–67, 1995), which contains the β-lactamase gene and promoter flanked by BamHI sites was similarly digested with BamHI and the insert corresponding to the β-lactamase gene was purified by agarose electrophoresis. The gel-isolated fragments were ligated and used to transform *E. coli* DH5α and recombinants selected in the presence of tetracycline (10 μg/ml) and ampicillin (100 μg/ml). The resulting construct, designated pCH1B, was verified by restriction enzyme analysis.

Marker Exchange/Forced Recombination

Cosmid pCH1B was transferred into *A. tumefaciens* Chry5 using the triparental mating scheme with plasmid pRK2013 as the helper plasmid (Ditta et al., *Proc. Natl. Acad. Sci.* (USA), 77: 7347–7351, 1980). Transformed bacterium were selected in the presence of rifampicin (100 μg/ml) and carbenicillin (100 μg/ml). The resulting strain, designated Chry51B, is also tetracycline resistant. This strain presumably contains both pCH1B and intact pTiChry5. The incompatible plasmid pPH1JI (Hirsch and Berenger, Plasmid 12: 139–141, 1984), containing the IncP RK2 ori, was next transferred into Chry51B and recombinants identified by simultaneous selection on LB agar containing rifampicin (100 μg/ml), carbenicillin (100 μg/ml) and gentamicin (40 μg/ml), the latter being the selection marker for pPH1JI. This selection provided clones that had undergone the intended double recombination event. The sensitivity of certain of the resultant clones to tetracycline (10 μg/ml) was tested, to verify that the pLAFR1 cosmid sequences had been lost in the recombination event. A clone that is resistant to gentamicin, carbenicillin and rifampicin, but sensitive to tetracycline was selected and designated *A. tumefaciens* KYRT1. The identity of the recombinant is further verified by Southern analysis of the Ti plasmid.

Stem and Leaf Inoculations

To test KYRT1 for loss of tumorigenicity, tobacco and tomato plants were inoculated with *A. tumefaciens* KYRT1 and Chry5 (see below). Disarmed *A. tumefaciens* strain EHA105 (Hood et al., *J. Bacteriol.* 168(3): 1283–1290, 1986) and its wild-type progenitor A281, were used as controls. Five weeks after the inoculation, large tumors of comparable size had formed on 100% of the inoculation sites for *A. tumefaciens* Chry5 and A281. In contrast, no tumors formed on the inoculation sites for *A. tumefaciens* KYRT1 and EHA105. One tobacco plant inoculated with KYRT1 did, however, show a small amount of blister, which may have been due to environmental contamination or by a non-agrobacterial callus formation. These results, then, indicate that the homologous recombination event in *A. tumefaciens* KYRT1 effectively removed the capacity for tumor formation in that bacterium.

To further confirm the loss of tumorigenicity in *A. tumefaciens* strain KYRT1, a GUS-INT construct was used for the transformation of tobacco leaves via Chry5, KYRT1 and EH105. As expected, tumorigenic strain Chry5::GUS-INT formed calli along the cut edges of inoculated leaves. In medium containing the hormones cytokinin (BAP) and auxin (IAA), strain KYRT1::GUS-INT and EHA105::GUS-INT formed calli at the inoculation sites, whereas there was no callus formation in the absence of these hormones. Moreover, calli and plantlets from calli inoculated with KYRT1::GUS-INT were positive for GUS as indicated by histochemical staining. These results indicate that *A. tumefaciens* KYRT1 has maintained a functional vir region, and can transfer foreign T-DNA containing heterologous genes, from introduced binary vectors.

Stem Inoculation Assay

Stems from two-month old tobacco (cv. Ky14) and three-week old tomato (cv. "Big Boy") were inoculated with wild-type *A. tumefaciens* Chry5, KYRT1, A281 and EHA105 (which is a disarmed strain A281 as an avirulent control). Two day old cultures were suspended to a density of ca. $10^8$ cells/ml in phosphate buffered saline (PBS), and applied with a 3 cm$^3$ syringe through a 17-gauge needle. The lower leaves of the tobacco plant were removed and the exposed regions were inoculated in two internodes, on opposite sides of the stem. The stem was scratched with a needle, making a ca. 3 mm wound, and the bacterial suspension was applied as a droplet to the freshly-made wound. Tomato plants are inoculated by piercing the stem with the needle, at two internodes, and applying a droplet of bacterial suspension at each of the wound openings. Plants were maintained under greenhouse conditions and fertilized weekly with a N-P-K (20:20:20) fertilizer. Tumor formation was scored by calculating the size of the tumor surface 5 weeks after inoculation.

Tobacco Leaf Transformation

A binary plasmid was conjugated into Chry5, KYRT1 and EHA105 by triparental mating as discussed above. The Km-resistant plasmid contains the GUS-intron gene in pBl121 (Clonetech, Inc.). Strains containing the binary plasmid were selected by resistance to kanamycin (100 μg/ml). The *A. tumefaciens* strains were used to inoculate excised leaves of aseptically grown, one month old tobacco (cv. Ky160) seedlings. Two day bacterial cultures in 5 ml LB medium containing rifampicin (100 μg/ml) and kanamycin (100 μg/ml) were twice centrifuged and resuspended in 5 ml LB without antibiotics. Tobacco leaves are dipped into the bacterial suspension and either halved or quartered. Leaf sections are transferred to modified Murashige and Skoog medium containing 3% sucrose and the hormones indoleacetic acid (1 mg/L) and benzyladenine (10 μM). After three days incubation, the leaf sections are washed in sterile water, blotted dry on sterile paper towels and transferred either to TOM medium (containing hormones) or T-medium (TOM medium lacking hormones), containing mefoxin (500 mg/L) and kanamycin (300 mg/L). Leaf explants were transferred to fresh medium after an additional three days and thereafter every seven days.

Soybean Cotyledonary Node Explant Assays

Soybean seedling cotyledonary node explants were inoculated with KYRT::GUS-INT as a test for stable transformation of soybean. Disarmed *A. tumefaciens* strains GV3850 and EHA105, also containing GUS-INT were also assayed for comparative purposes. On average, explants inoculated with KYRT1::GUS-INT produced three times as many GUS-positive sectors (as judged by histochemical staining) as explants inoculated with either GV3850::GUS-INT or EHA105::GUS-INT. Based upon chi-square analysis, the difference between KYRT1 and GV3850 was significant at the 0.01 level, while that between KYRT1 and EHA105 was significant at the 0.05 level. These results demonstrate the clear improvement in transformation efficiency using *A. tumefaciens* strain KYRT1.

Soybean Cotyledonary Nodes

Cotyledonary node cultures were initiated from 3 day-old seedlings of soybean (cv. Fayette) (Townsend, J. A., International Patent Application No. WO 94/02620, 1994). *A. tumefaciens* strains KYRT1, EHA105 and GV3850 containing GUS-INT were grown as 1 ml cultures for two days in LB medium containing rifampicin (100 μg/ml) and kanamycin (100 μg/ml). *A. tumefaciens* GV3850 and KYRT1 growth medium also contains carbenicillin (100 μg/ml). These two-day cultures are used to inoculate 100 ml cultures, which are then grown overnight to mid-log phase. Cultures were pelleted and resuspended as two 10 ml aliquots in co-cultivation medium (Gamborg B5 medium containing 44 μM benzyladenine, 0.5 μM indolebutyric acid and buffered to pH 5.5 with 10 mM MES) containing acetosytingone (100μM). Three day-old seedlings were prepared (Veluthambi et al., *J. Bacteriol.* 170(4): 1523–1532, 1988; Townsend, International Patent Application No. WO 94/02620, 1994), and immersed in the bacterial suspension for one hour. Explants are cultured adaxial side up on solidified co-cultivation medium for three days, after which they are washed with sterile water, blotted dry and cultured adaxial side down on counter-selection medium (Gamborg B5 containing benzyladenine (5 μM), indolebutyric acid (0.5 μM) and buffered to pH 5.7 with 3 mM MES), containing mefoxin (500 mg/L) and vancomycin (200 mg/L). After one week, the explants are transferred to counter-selection medium containing mefoxin (250 mg/L), vancomycin (100 mg/L) and kanamycin (100 mg/L) and sub-cultured every two to three weeks thereafter. Six weeks after inoculation, shoot masses that form at the base of the cotyledon are harvested, cut into ca. 1.5 mm thick sections and assayed for GUS activity by histochemical staining (Jefferson, *Plant Mol. Biol. Rep.* 5: 387–405, 1987). On average, explants inoculated with KYRT1::GUS-INT produced three times as many GUS-positive sectors as explants inoculated with either GV3850::GUS-INT or EHA105::GUS-INT. The difference between KYRT1 and GV3850 was significant to the 0.1 level based on chi-square analysis whereas the difference between KYRT1 and EHA105 was significant at the 0.05 level, demonstrating that KYRT1 is indeed an improved disarmed vector for the transformation of soybean cotyledonary node tissue.

The above-embodiments of the invention are meant to be illustrative and are not to be construed as limiting on the broad claims appended hereto. Obvious variants of the embodiments disclosed are readily recognized by those skilled in the art and are meant to be within the scope and spirit of the claims.

Each of the publications and patents cited herein are expressly incorporated herein by reference thereto.

We claim:

1. A disarmed *Agrobacterium tumefaciens* strain KYRT1, having ATCC Accession No. 202167.

2. A method of producing a transgenic plant comprising the steps:
   (a) introducing a binary vector comprising a gene of interest into the disarmed *Agrobacterium tumefaciens* strain of claim 1 to produce a recombinant *A. tumefaciens*;
   (b) contacting said recombinant *A. tumefaciens* of with at least one site on a plant tissue, wherein said site comprises a wound site, and said plant tissue is selected from the group consisting of embryogenic, cotyledonous and somatic tissue; and
   (c) culturing said plant tissue to allow regeneration of said tissue into a transgenic plant.

3. The method of producing a transgenic plant according to claim 2, wherein said plant tissue is a dicotyledonous plant tissue.

4. The method of producing a transgenic plant according to claim 3, wherein said dicoytyledonous plant tissue is soybean (*Glycine max*) plant tissue.

5. The method of producing a transgenic plant according to claim 3, wherein said dicotyledonous plant tissue is from a conifer or from a genus selected from the group consisting of Medicago, Lycopersicon, Brassica, Cucumis, Solanum, Juglans, Gossypium, Malus, Vitis, Antirrhinum, Populus, Fragaria, Arabidopsis, Picea, Capsicum, Chenopodium, Dendranthema, Pharbitis, Pinus, Pisum, Oryza, Glycine, Pseudotsuga, Kalanchoe, Beta, Helianthus and Nicotiana.

* * * * *